US006988995B2

(12) United States Patent
Zhou et al.

(10) Patent No.: US 6,988,995 B2
(45) Date of Patent: Jan. 24, 2006

(54) METHOD AND SYSTEM FOR DETECTING THE EFFECTS OF ALZHEIMER'S DISEASE IN THE HUMAN RETINA

(75) Inventors: Qienyuan Zhou, Del Mar, CA (US); Michael J. Sinai, Carlsbad, CA (US); John C. Moore, Encinitas, CA (US); William Wong, Encinitas, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 666 days.

(21) Appl. No.: 10/260,927

(22) Filed: Sep. 30, 2002

(65) Prior Publication Data

US 2004/0064064 A1   Apr. 1, 2004

(51) Int. Cl.
*A61B 13/00* (2006.01)

(52) U.S. Cl. ..................... 600/558; 356/484
(58) Field of Classification Search ............... 600/558, 600/588; 356/484, 367; 351/221
See application file for complete search history.

(56) References Cited

U.S. PATENT DOCUMENTS

| | | | |
|---|---|---|---|
| 5,303,709 A | 4/1994 | Dreher et al. ............... | 128/665 |
| 5,787,890 A | 8/1998 | Reiter et al. ................ | 128/665 |
| 6,112,114 A | 8/2000 | Dreher ....................... | 600/476 |
| 6,137,585 A | 10/2000 | Hitzenberger et al. ...... | 356/484 |
| 6,293,674 B1 * | 9/2001 | Huang et al. ............... | 351/221 |
| 6,356,036 B1 | 3/2002 | Zhou .......................... | 315/215 |
| 6,704,588 B2 * | 3/2004 | Ansari et al. ............... | 600/319 |

OTHER PUBLICATIONS

Vapnik, Vladimir N., "An Overview of Statistical Learning Theory" *IEEE Transactions on Neural Networks*, vol. 10, No. 5, Sep. 1999.
Blanks, Janet C., Torigoe, Yasuhiro, Hinton, David R., and Blanks, Robert H.I., "Retinal Pathology in Alzheimer's Disease. I. Ganglion Cell Loss in Foveal/Parafoveal Retina" *Neurobiology of Aging*, vol. 17, No. 3, pp. 377-384 (1996).
Blanks, Janet C.; Schmidt, Susan Y.; Torigoe, Yasuhiro; Porrello, Kathryn V.; Hinton, David R. and Blanks, Robert H.I. "Retinal Pathology in Alzheimer's Disease. II. Regional Neuron Loss and Glial Changes in GCL" *Neurobiology of Aging*, vol. 17, No. 3, pp. 385-395 (1996).

(Continued)

*Primary Examiner*—Charles Marmor
*Assistant Examiner*—Fangemonique Smith
(74) *Attorney, Agent, or Firm*—Stallman & Pollock LLP

(57) ABSTRACT

A system for the in vivo detection of the effects of AD in the interior of an eye. A scanning polarimeter, including a residual retardance canceling system and an improved anterior segment retardance compensator, produces an optical analysis signal representing the birefringence of the retinal nerve fiber layer (RNFL) structures of the eye. The birefringence data is more accurate because of compensation for anterior segment birefringence and residual birefringence of optical components, such as, for example, the beam splitters, lenses, scanners and retarders. An electrical analysis signal representing a large (20 by 40 degrees) retardance map is produced and evaluated by an artificial neural network to produce an analysis classification signal representing the contribution of Alzheimer's disease to the birefringence of the retinal layer corresponding to the relationship of the electrical analysis signal to an analysis signal database.

18 Claims, 3 Drawing Sheets

OTHER PUBLICATIONS

Hedges III, Thomas R.; Galves, Rosalba Perez; Speigelman, Donna; Barbas, Nancy R.; Peli, Eli and Yardley, Christine J. "Retinal Nerve Fiber layer Abnormalities in Alzheimer's Disease" *ACTA Ophthalmologica Scandinavica*, 74:271-275 (1996).

Kergoat, Hélène; Kergoat, Marie-Jeanne; Justino, Lisette; Robillard, Alain; Bergman, Howard and Chertkow, Howard "Normal Optic Nerve Head Topography in the Early Stages of Dementia of the Alzheimer Type" *Dementia and Geriatric Cognitive Disorders*, 12:359-363 (2001).

Kergoat, Hélène; Kergoat, Marie-Jeanne; Justino, Lisette; Chertkow, Howard; Robillard, Alain; Bergman, Howard "An Evaluation of the Retinal Nerve Fiber Layer Thickness by Scanning Laser Polarimetry in Individuals with Dementia of the Alzheimer Type" *ACTA Ophthalmologica Scandinavica* 79:187-191 (2001).

* cited by examiner

METHOD AND SYSTEM FOR DETECTING THE EFFECTS OF ALZHEIMER'S DISEASE IN THE HUMAN RETINA

CROSS-REFERENCES TO RELATED APPLICATIONS

This application is related by common inventorship and subject matter to the commonly-assigned patent application Ser. No. 10/160,808 filed on May 31, 2002, entitled A METHOD AND SYSTEM FOR CANCELING SYSTEM RETARDANCE ERROR IN AN OPHTHALMOLOGICAL POLARIMETER and entirely incorporated herein by this reference.

BACKGROUND OF THE INVENTION

1. Field of the Invention

This invention relates generally to ophthalmological polarimeter systems for measuring retinal nerve fiber layer (RNFL) retardances and more particularly to an ophthalmological system for detecting the effects of Alzheimer's disease in the human retina.

2. Description of the Related Art

Alzheimer's disease (AD) was first identified and named in 1906 by Dr. Alois Alzheimer, a German neuropathologist. He had been treating a middle-aged female client who presented symptoms of memory loss and disorientation. Five years later the patient died after suffering hallucinations and symptoms of dementia. The manifestations and course of the disease were so unusual that Dr. Alzheimer was unable to classify the disease into any existing category. Postmortem examination of the brain revealed lesions and distortions, including neuritic plaques and neurofibrillary tangles. AD is characterized by severe cognitive impairment that is insidious, progressive, irreversible and eventually fatal. AD accounts for roughly 60–80 percent of all dementia patients in the United States. It proceeds in stages, gradually destroying all cognitive functions. AD generally affects older men and women, with 75 the average age of onset. While the age range for onset is from 52 to 89 years, the disease is also seen (rarely) in younger people. The risk increases with age and the death rate for people with AD is twice that among those of the same age without the disease.

Practitioners in the art have long sought methods for the identification of conditions associated with the early stages of AD to permit early intervention where possible. A definitive diagnosis of Alzheimer's can only be made during an autopsy. The presence of amyloid plaques and neurofibrillary tangles confirm the disease process. In the present art, a probable diagnosis relies on the medical history, physical examination, diagnostic studies and assessment for the presence of delirium and depression following a full mental status evaluation. The observation of signs and symptoms and the ruling out of other disease processes is relied upon for the diagnosis in the absence of pathology reports. The earlier the diagnosis is made, the greater the benefit in managing the clinical course of the illness, which may include measures for protection against head injury or repeated concussions and protection from toxic exposures such as aluminum. Nonsteroidal anti-inflammatory drugs used continuously for more than two years may delay the onset or reduce the likelihood of developing AD, and antioxidants, particularly vitamin E, may reduce oxidative stresses known to contribute to the evolution of AD. But no cure for AD is known in the art and no AD diagnosis can be definitively confirmed without a postmortem autopsy.

The issue of whether the retinal nerve fiber layer (RNFL) is affected in any way by AD is unsettled. Several practitioners report finding the presence of significant central retinal ganglion cell loss to be correlated with the presence of AD, as reported by, for example, Blanks et al. [Blanks J C, Torigoe Y, Hinton D R, Blanks R H, "Retinal Pathology in Alzheimer's Disease I: Ganglion Cell Loss in Foveal/Parafoveal Retina," *Neurobiol. Aging*, 17, 377–84 (1996)] and Blanks et al. [Blanks J C, Schmidt S Y, Torigoe Y, Porrello K V, Hinton D R, Blanks R H, "Retinal Pathology in Alzheimer's Disease II: Regional Neuron Loss and Glial Changes in GCL," *Neurobiol. Aging*, 17, 385–95 (1996)]. Blanks et al. showed experimental evidence of an overall decrease of 25% in total numbers of neurons in the ganglion cell layer (GCL) of the central retina in AD patients compared to a control sample. Postmortem confirmation of the AD diagnosis was obtained in all cases. Detailed postmortem analyses of GCL neurons at various sites in the foveola showed that the greatest decrease in neuronal density (e.g., 43%) occurred in the central 500 micron foveal region while neuronal losses of 24% to 26% were found further out to 1,500 microns. The temporal region of the central retina was most severely affected with up to 52% loss in neuronal density compared to milder losses in the nasal regions. Close agreement (within 15%) was found between fellow eyes and all neuron sizes were affected similarly in AD patients. The neuron sizes in control retinas decreased with age, a correlation not found in retinas from AD patients.

Several other practitioners, like Blanks et at, have published autopsy studies providing persuasive evidence of the involvement of the retina nerve layer in the AD process, which has induced other practitioners in the art to propose methods for the in vivo examination and analysis of the GCL to identify features related to AD in the earlier stages, which is more precisely denominated Dementia of the Alzheimer's Type (DAT) because it is unconfirmed by autopsy. For example, Hedges et al. [Hedges III T R, Galves R B, Speigelman D, Barbas N R, Peli E, and Yardley C J, "Retinal Nerve Fiber Layer Abnormalities in Alzheimer's Disease," *Acta Ophthalmol. Scand.* 1996: 74, 271–75] employed retinal photographs to identify "abnormalities in two groups of living patients; those diagnosed with AD and a control group without an AD diagnosis. Although Hedges et al. find evidence of ganglion cell degeneration related to AD, their method exhibited limited usefulness, especially in advanced cases of AD, because of the difficulty in obtaining and evaluating RNFL photographs. There was some disagreement between observers regarding the quality and frequency of abnormalities that reflected the difficulty in obtaining precise photographs of RNFL features.

Other practitioners report finding no consistent RNFL degeneration when monitoring in vivo DAT patients. For example, Kergoat et al. [Kergoat H, Kergoat M J, Justino L, Robillard A, Bergman H, Chertkow H, "Normal Optic Nerve Head Topography in the Early Stages of Dementia of the Alzheimer Type," *Dement. Geriatr. Cogn. Disord.* 2001: 12, 359–63] found no difference between early-stage DAT patients and age-equivalent control subjects when using in vivo measurements of nerve head topography obtained with a Heidelberg retina tomograph. Similarly, in another study, the same practitioners concluded that the RNFL is not altered by the presence of DAT in the early stages according to data obtained from laser polarimetry measurements [Kergoat H, Kergoat M J, Justino L, Chertkow H, Robillard A, Bergman H, "An Evaluation of the Retinal Nerve Fiber Layer Thickness by Scanning Laser Polarimetry in Individuals with Dementia of the Alzheimer Type,"*Acta Ophthalmol.*

Scand. 2001: 79, 187–91]. These in vivo findings from Kergoat et al. are inconsistent with the postmortem findings from several other practitioners, perhaps because of the earlier AD stage or an unidentified source of measurement error. Kergoat et al. examined only the first 15 degrees of the field of view of the fovea.

The scanning laser polarimetry art is described in the commonly-assigned U.S. Pat. Nos. 5,303,709, 5,787,890, 6,112,114, and 6,137,585, all of which are entirely incorporated herein by reference. The scanning laser polarimeter is a diagnostic device that measures the thickness of the RNFL by measuring the retardance of laser light in the RNFL layer and correlating the retardance to RNFL thickness according to well-known principles. The RNFL thickness measurements thus obtained are subject to significant errors arising from (a) uncompensated anterior eye segment birefringence and (b) uncompensated system birefringence in the optical measurement path, including the residual retardance of optical elements. These errors vary unpredictably over the foveal measurement region and tend to mask the RNFL characteristics most useful in identifying the subtle effects of disease processes, such as AD. In particular, two recent improvements have eliminated much of these measurement errors; the anterior segment retardance compensator and the residual retardance canceling system.

The commonly-assigned U.S. Pat. No. 6,356,036 B1, entirely incorporated herein by reference, discloses an improved anterior segment retardance compensator based on an improved polarimetric method for measuring complex (magnitude and axial orientation) birefringence in both the anterior and the posterior segments of the human eye. The anterior segment includes essentially the combined birefringence of the cornea and the crystalline lens, and the posterior segment includes regions at the fundus. The complex birefringence of the anterior segment is first determined so that it can be canceled by a variable retarder to eliminate this source of error in complex posterior segment birefringence measurements. The procedure improves accuracy by using the patient's Henle fiber layer (instead of the lens posterior surface) as a reference surface for determining complex anterior segment birefringence. The above-cited patent application discloses a residual retardance canceling system that eliminates the other important source of measurement error by introducing a method for averaging multiple retardance measurement samples to cancel the effects of residual system birefringence in the diagnostic path. The above-described Kergoat et al. studies apparently did not use either of these two improvements.

Beyond complex retardance measurement error, another problem with attempting to identify the effects on RNFL characteristics related to disease processes such as AD is the evaluation of the RNFL measurement data, which may include a large two-dimensional array of RNFL thickness and topology data, for example. These data must be compared with another similarly large array of data measured for another group of control subjects. Some early practitioners attempted to perform this evaluation simply by studying photographs to ascertain similarities and differences; a process so subjective as to be nearly useless for finding consistent results. Even expert systems for evaluating patterns and relationships in the measurement data arrays cannot alone discover new and unsuspected patterns or relationships in the data. Efforts to generalize expert systems have encountered a number of problems. For example, as the system complexity increases, the system demand for computing resources exceeds available capacity. Expert systems are generally feasible only when narrowly confined and cannot identify new patterns in large data arrays.

Other adaptive systems such as artificial neural networks (ANNs) may be used to discover new and unsuspected patterns or relationships in measured data by first "learning" with "training data" to recognize features and patterns present in the training data before evaluating other data for similar features. ANNs offer a different approach to problem solving and they are sometimes called the sixth generation of computing. They try to provide a tool that both programs itself and learns on its own. ANNs are structured to provide the capability to solve problems without the benefits of an expert and without the need of programming. They can seek patterns in data that no one knows are there.

Another useful adaptive system is the support vector machine (SVM), which is a learning machine that can perform binary classification and regression estimation tasks. The SVM performs structural risk minimization by creating a classifier with minimized Vapnik-Chervonenkis (VC) dimension. If the VC dimension is low, the expected probability of error is low as well, which yields a good generalization.

SVMs non-linearly map their n-dimensional input space into a high-dimensional feature space wherein a linear classifier is constructed. Two results make this approach successful. The generalization ability of the SVM depends only on the VC dimension of the implemented function set and not on the feature space dimensionality. Any function that describes the data well and belongs to a set of low VC dimension can generalize well regardless of the feature space dimension. Construction of the classifier requires only the evaluation of an inner product between two training data vectors, so an explicit (and time-consuming) mapping into the high-dimensional feature space is not necessary. In Hilbert space, for example, inner products have simple kernel representations that can be quickly and easily evaluated. The SVM is well known in the adaptive system art and is described by V. N. Vapnik in a textbook [*The Nature of Statistical Learning Theory*, Springer-Verlag, N.Y., ISBN 0-387-94559-8, 1995] and in a recent paper [Vapnik, V N, "An Overview of Statistical Learning Theory," *IEEE Trans. Neural Networks*, vol. 10, no. 5, 1999]. These adaptive system tools have not been employed to assist with the evaluation of the effects on the RNFL of AD.

There is accordingly a clearly-felt need in the art for a method and system that can measure RNFL features with sufficient accuracy to identify subtle characteristic patterns that are suitable for automated classification to identify the effects of Alzheimer's disease in the earlier in vivo stages. The unresolved problems and deficiencies are clearly felt in the art and are solved by this invention in the manner described below.

SUMMARY OF THE INVENTION

This invention solves the retinal nerve fiber layer (RNFL) feature data acquisition and classification problem described above by introducing a laser scanning polarimeter system, including a residual retardance canceling system and an improved anterior segment retardance compensator, to acquire accurate RNFL feature data over an extended foveal region and including an adaptive pattern classification system trained with a normative database to classify the accurate RNFL feature data and to detect the effects of Alzheimer's disease (AD).

It is a purpose of this invention to provide an ophthalmological system and method for measuring the complex birefringence of structural elements in the eye with the improved accuracy necessary to identify the effects of AD in the RNFL.

It is a feature of this invention that measurements made over a relatively large 20 by 40 degree region that includes both the fovea and the peripapillary retina, thereby generating a much larger feature map. It is an advantage of this invention that the data acquired for the larger feature map has less error because of the compensation of anterior segment birefringence and residual birefringence of optical components, such as, for example, the beam splitters, lenses, scanners and retarders.

In one aspect, the invention is a method for detecting the effects of Alzheimer's disease (AD) in the interior of an eye having a pupil, including the steps of (a) producing an optical analysis signal representing the birefringence of the biological structures between the exterior of the eye and the posterior surface of the retinal layer in the interior of the eye, (b) adjusting the optical analysis signal to cancel the effects of birefringence in the biological segments anterior to the retinal layer, (c) passing the adjusted optical analysis signal through one or more optical elements exterior to the eye, (d) producing an electrical analysis signal representing the adjusted optical analysis signal, (e) processing the electrical analysis signal to cancel the effects of residual birefringence in the one or more optical elements exterior to the eye, and (f) producing an analysis classification signal representing the contribution of Alzheimer's disease to the birefringence of the retinal layer corresponding to the relationship of the electrical analysis signal to an analysis signal database.

In another aspect, the invention is a system for detecting the effects of AD in the interior of an eye having a pupil, including a scanning polarimeter for producing an optical analysis signal representing the birefringence of the biological structures of the eye between the exterior of the eye and the posterior surface of the retinal layer in the interior of the eye, a variable retarder for adjusting the optical analysis signal to remove the effects of birefringence of the biological segments anterior to the retinal layer, one or more optical elements exterior to the eye for directing the optical analysis signal, a detector for producing an electrical analysis signal representing the adjusted optical analysis signal, a processor coupled to the detector for canceling the effects on the electrical analysis signal of residual birefringence in the one or more optical elements exterior to the eye, and an artificial neural network for producing an analysis classification signal representing the contribution of Alzheimer's disease to the birefringence of the retinal layer corresponding to the relationship of the electrical analysis signal to an analysis signal database.

The foregoing, together with other objects, features and advantages of this invention, can be better appreciated with reference to the following specification, claims and the accompanying drawing.

BRIEF DESCRIPTION OF THE DRAWINGS

For a more complete understanding of this invention, reference is now made to the following detailed description of the embodiments as illustrated in the accompanying drawing, in which like reference designations represent like features throughout the several views and wherein.

DETAILED DESCRIPTION OF THE EMBODIMENTS

As used herein, the term polarization "biasing" generically covers all types of polarization changes, including the rotation of the optical axis of polarized light, the change of linear to elliptically or circularly polarized light or vice-versa, and any combination of these. The term "polarimetry" refers to techniques for determining the polarization "bias" of a light beam. The term "polarimeter" refers to devices for performing polarimetry. The terms "spatially resolved retinal polarimetry" and "spatially resolved retinal polarimeter" refer to the technique and device for performing polarimetry, point by point, on the retina. The term "retardance map" refers to a two-dimensional display of retardance distribution measured with a spatially resolved polarimeter. The term "corneal birefringence" means anterior segment birefringence, including contributions of the lens in addition to the cornea; and the term "corneal compensator" is used to describe a device for neutralizing the birefringence of the anterior segment of the eye, such as a variable retarder.

Figure 1:
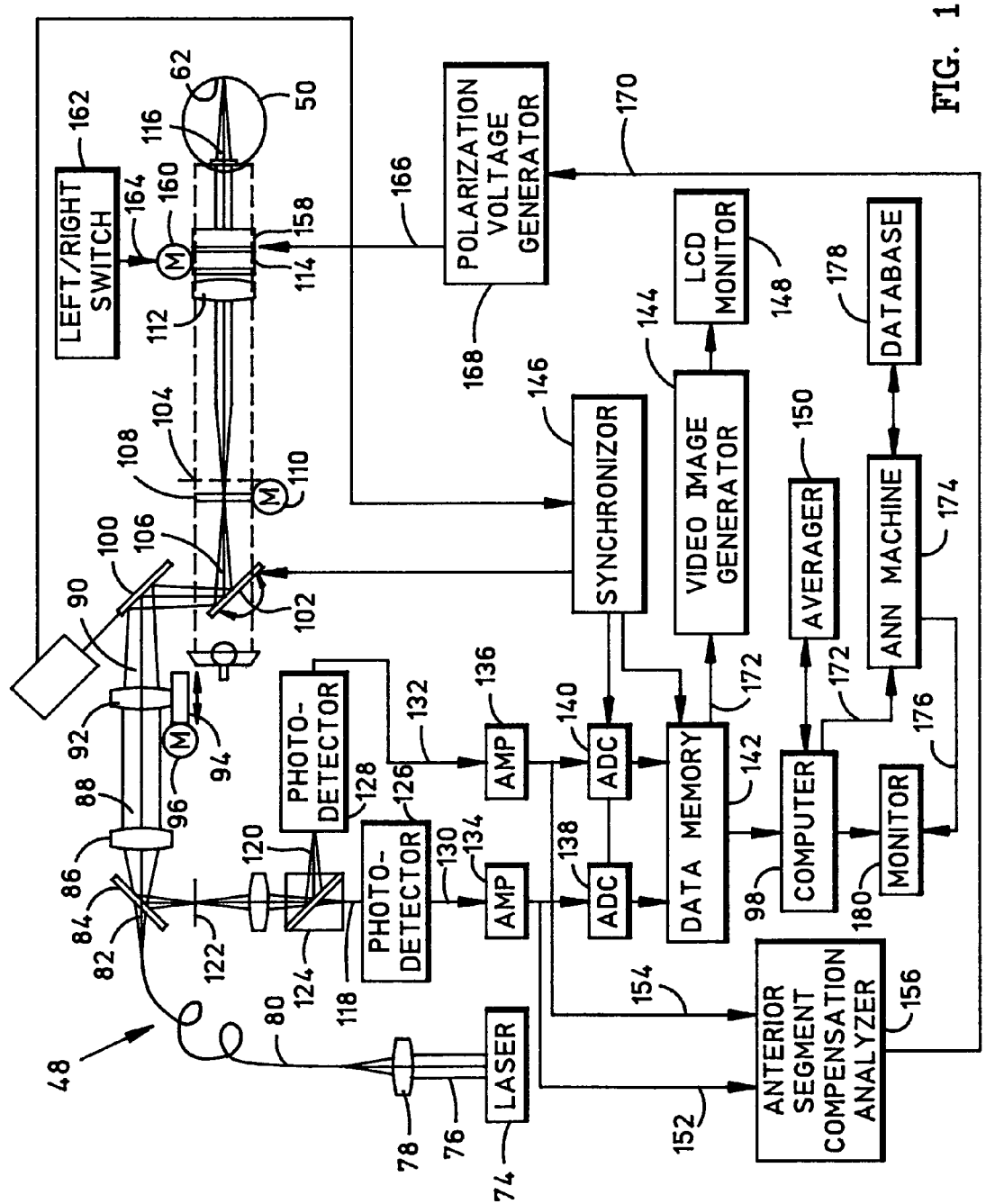
FIG. 1 is a block diagram illustrating an exemplary embodiment of the ophthalmological system of this invention.
Figure 2B:
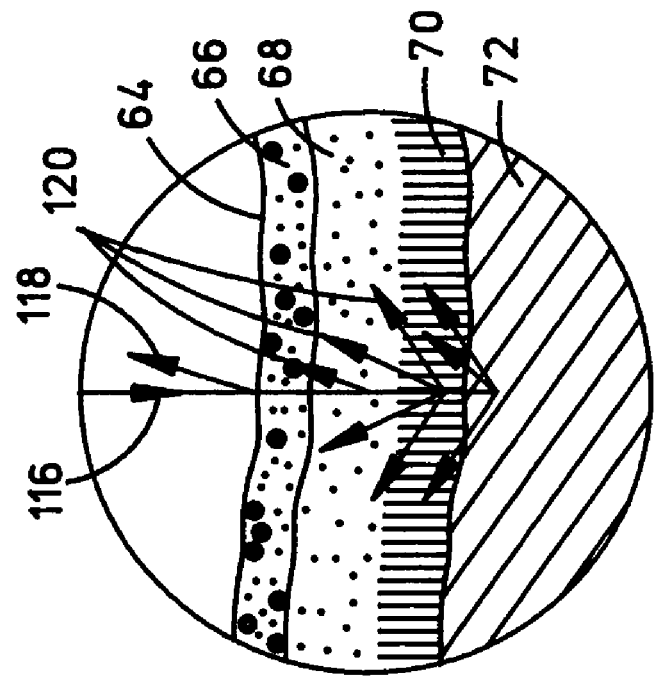
FIGS. 2A and 2B illustrate the elements of the eye related to the method and system of this invention.
Figure 2A:
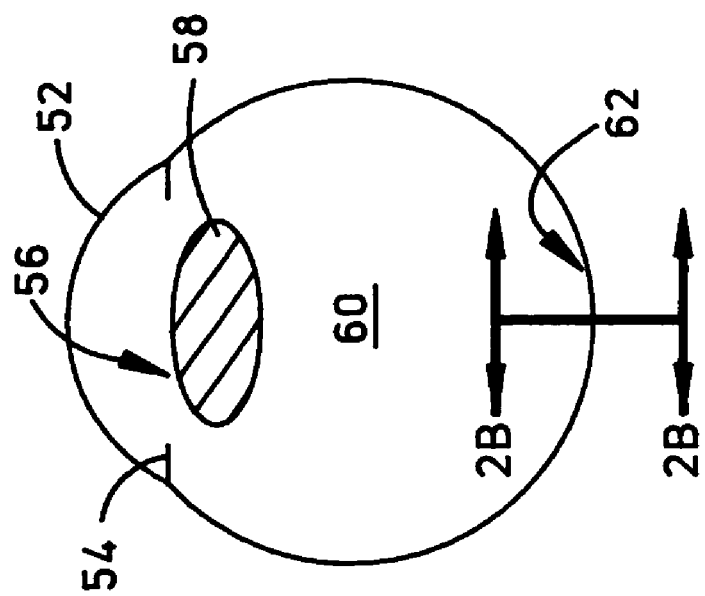

FIG. 1 is a block diagram illustrating the ophthalmological system 48 of this invention for analyzing the eye 50, which is described in FIGS. 2A and 2B. Eye 50 includes the cornea 52 as the foremost, transparent portion of eye 50, behind which is the iris 54 (having a pupil 56) and the lens 58. The interior 60 of eye 50 is filled with vitreous humor. The back of eye 50 includes the retina (shown in cross-section in FIG. 2B), composed of many layers or structures, including, in the area of the fundus 62, the internal limiting membrane 64, the retinal nerve fiber layer (RNFL) 66, the receptor system 68, the retinal pigment epithelium 70, the choroid 72 and the Henle fiber layer (not shown), which is generally located at the level of RNFL 66. All structures forward of membrane 64 are considered part of the anterior segments of eye 50 for purposes of this disclosure.

System 48 is suitable for analyzing a structure in eye 50 to provide, for example, an image map of the thickness of RNFL 66 or the Henle fiber layer (not shown). In accordance with this invention, a polarized diode laser 74 of wavelength 780 nm provides a source of the optical diagnostic signal 76. Although light of any wavelength that passes the ocular media may be used, a diode laser wavelength 780 nm is an excellent compromise between optical performance, patient comfort, and laser safety. Linearly-polarized optical diagnostic signal 76 is focused by the coupling lens 78 onto a polarization-maintaining, single-mode optical fiber 80. The diverging optical signal beam 82 emerging from optical fiber 80 impinges upon the beam splitter 84, which may be a non-polarizing beam splitter or a partially polarizing beam splitter. Because diverging optical beam 82 is substantially polarized parallel to the plane of incidence, about 85% of the signal impinging upon beam splitter 84 is transmitted through and collected by the lens 86 to produce a collimated optical beam 88. Collimated optical beam 88 is converged to a converging optical beam 90 by the focusing lens 92, which is mounted on a focus translation stage 94. A stepper motor 96 is used to move lens 92 under control of, for example, a computer 98.

Consequently, converging optical beam 90 is deflected by the resonant scanner 100 to generate a focused two-dimensional laser raster 104 having, for example, 256 lines distributed over a sample plane. At each point of the scan, in accordance with this invention, the scanned laser optical signal 106 penetrates a polarization rotator consisting of a half-wave plate 108 and the stepper motor-controlled drive mechanism 110. Half-wave plate 108 rotates the polarization axis of scanned converging optical signal 106 without geometrically rotating focused two-dimensional laser raster 104.

Focused two-dimensional laser raster 104 is focused (imaged) by the lens 112 onto fundus 62 of eye 50 through a variable retarder 114, cornea 52, pupil 56 and lens 58 (FIGS. 2A–2B). By moving focusing lens 92, focused raster scan pattern 104 may be imaged onto different layers of fundus 62. A small part of the illuminating optical beam 116 may be specularly reflected from internal limiting membrane 64 of fundus 62 to produce a weak specular reflection optical beam 118. The remainder of illuminating optical beam 116 penetrates the form-birefringent RNFL 66 and is partially reflected by the more-posterior retinal layers, thereby twice-passing RNFL 66 and forming the diffuse reflection optical beam 120. Because of the form-birefringent properties of RNFL 66, the state of polarization of the diffuse reflection optical beam 120 is changed with respect to the state of polarization of the illuminating optical beam 116.

Reflected optical beam 120 exits eye 50 through lens 58, pupil 56 of iris 54, and cornea 52, and travels back along substantially the same optical path as described above until it impinges upon beam splitter 84, where it is separated from diverging optical beam 82 in the usual manner. Lens 86 focuses reflected optical beam 120 onto the pinhole aperture 122, which is located at a plane conjugate to the exit aperture of optical fiber 80, the plane of focused two-dimensional laser raster 104, and the plane of fundus 62.

Reflected optical beam 120 passes through pinhole aperture 122 to a polarizing beam splitter 124 or a similar arrangement of polarizers and beam splitter. Polarizing beam splitter 124 transmits all light having a state of polarization identical to the state of polarization of diverging optical beam 82, thereby allowing it to be imaged onto a photo detector 126. Any light having a polarization different from the polarization of diverging optical beam 82 is reflected by beam splitter 124 and thereby imaged onto the second photo detector 128. The output signals 130 and 132 from photo detectors 126 and 128 are amplified by the amplifiers 134 and 136 and digitized by the analog-to-digital converters 138 and 140. The amplified and digitized outputs of the photo detectors 126 and 128 are then stored in a dual ported data memory 142, which is accessible by computer 98 and the video image generator 144.

A synchronizer 146 is triggered by the oscillating frequency of the resonant scanner 100 and produces the driving signal for the galvanometer scanner 102. In addition, synchronizer 146 controls the memory location address within data memory 142 so that each amplified and digitized output of each of photo detectors 126 and 128 can be correlated with the scan position of resonant scanner 100 and galvanometer scanner 102 at the time of data sampling. In one embodiment, for example, 256 data samples of each of photo detectors 126 and 128 are acquired, digitized, and stored along one horizontal scan line, and 256 scan lines at gradually changing vertical positions are acquired before the scan procedure is repeated. Video image generator 144 immediately reads the data samples from dual ported data memory 142 and produces a video image that may be displayed on a liquid crystal display device 148, for example.

Any residual birefringence of the optical components, such as, for example, the beam splitters, lenses, scanners and retarders, is canceled in accordance with the method of this invention as follows. In ophthalmological system 48, a plurality of signal samples are collected in data memory 142 for each scan position and the extrema (maxima and minima) are selected and averaged in the averager 150 over a 180-degree range of rotation of half-wave plate 108 to obtain the mean signal extrema $[\bar{S}_{max}, \bar{S}_{min}]$ representing the retardance of the scan position in the structure at fundus 62, unbiased by the system birefringence including the birefringence of half-wave plate 108. The rotation of half-wave plate 108 over the necessary range may proceed concurrently with the two-dimensional scan provided by resonant scanner 100 and galvanometer scanner 102, thereby providing for each scan position in raster 104 a series of samples over the 180-degree rotation of half-wave plate 108. Signal extrema are determined and averaged according to this invention for each of the scan positions in raster 104.

In parallel with the data acquisition process described above, the amplified output signals 152 and 154 of photo detectors 126 and 128 are analyzed by the anterior segment compensation analyzer 156. Variable retarder 114 may include, for example, a combination of a plurality of fixed optical retarders, including a layer of liquid crystal material 158. Variable retarder 114 can be rotated about its axis by a motor 160. A proximity switch 162 automatically detects the position of the examination device (not shown) to determine if the left or right eye is being examined. The left/right eye signal 164 from proximity switch 162 is used to control the motor 160, which rotates the variable retarder 114 so that the variable retarder optic axis substantially coincides with the measured fast axis of the birefringence of the anterior segments (including cornea 52) of eye 50.

A varying voltage signal 166 is generated by the polarization voltage generator 168 and applied to variable retarder 114 to vary the polarization properties of liquid crystal layer 158 and, thereby, the state of polarization of an optical beam passing through variable retarder 114. Other fixed or variable retarders or combinations thereof, such as, for example, a Pockets cell, a Kerr cell, a Soleil-Babinet retarder, combinations of rotating fixed retarders, and the like, may be employed in similar fashion to liquid crystal layer 158 described for this exemplary embodiment.

A closed loop circuit 170 changes output 166 from polarization voltage generator 168 until output signal 130 from photo detector 126 is maximized and output signal 132 from photo detector 128 is minimized. In this state, the amount of polarization bias introduced to an optical signal when passing through anterior polarization compensator 114 effectively cancels the polarization bias introduced to the same optical beam when passing through the anterior segments of eye 50. Once the anterior segment polarization effects are canceled, signal outputs 130 and 132 from photo detectors 126 and 128 represent only the birefringence of the posterior retinal layers and therefore may be used to represent the topography or the thickness of RNFL 66, for example. Although anterior segment retardance varies somewhat from point-to-point across the cornea, only one such point is penetrated by the diagnostic beam in a single scanning session and a single correction value is sufficient for each scan. Anterior segment birefringence compensation in this fashion is automatic, adjustment is needed only once at the beginning of a scanning session, and compensation need not be updated during a single scan.

The RNFL image data array 172 stored in data memory 142 are also available to the artificial neural networks (ANN) machine 174, which may be implemented as a software object in computer 98, for example, or independently in hardware or software. Raster 104 may, for example, provide for 64K data samples (256 by 256) arrayed over a 20 by 40 degree region of the retina. These 64K data samples may be acquired in about 33 ms so the measurements may be repeated several times to add sufficient redundancy to the scan data to support any useful statistical error correction procedure or to identify and eliminate distortion arising from uncontrolled eye movement. In the manner described above, each data sample is corrected for anterior segment birefringence and residual birefringence of optical components, such as, for example, the beam splitters, lenses, scanners and retarders, and stored in data memory 142 as a data array representing a video image that may be displayed on a liquid crystal display device 148. This RNFL image data array 172 of, for example, 64K data samples of RNFL thickness over a 20 by 40 degree region of the retina, can be presented to ANN machine 174, which produces an analysis classification signal 176 representing the contribution of Alzheimer's disease to the birefringence of the retinal layer corresponding to the relationship of 64K RNFL image data array 172 to a database 178 of similar data arrays obtained from other eyes. Analysis classification signal 176 may be reported on, for example, a monitor 180 if desired.

Before ANN machine 174 can be "trained" by, for example, a back propagation procedure known in the neural network art, to identify the contribution of AD to the birefringence of the retinal layer represented in data array 172, database 178 must be acquired by, for example, obtaining 64K RNFL image data arrays for a number of controls without any AD symptoms and a number of living patients with diagnoses of dementia of the Alzheimer type (DAT) and/or from the eyes of patients verified as suffering from AD by postmortem examination. The numbers of data array samples required may be established using any useful statistical sampling methodology known in the art. Once the necessary RNFL images are obtained, identified and stored in database 178 ANN machine 174 may then be "trained" to distinguish between the RNFL image data arrays in database 178 that are affected by AD and those without such effects. In an alternative embodiment, ANN machine 174 may include a support vector machine (SVM) that may be "trained" to identify a hyperplane in multidimensional feature space representing the optimal boundary between RNFL image data arrays from database 178 showing effects of AD and RNFL image data arrays from database 178 without such effects, for example. Such an SVM may be implemented within computer 98 as a software program module, for example.

It appears that the RNFL damage caused by AD is different, in location and pattern, from the damage noted in glaucoma patients. Glaucoma damage tends to be more peripheral in location, especially in the early stages that affect superior and inferior RNFL primarily. But AD damage is more concentrated in the central region, which is affected more than the peripheral RNFL. This distinction permits isolation of the contribution of AD to the birefringence of the RNFL.

Figure 3:
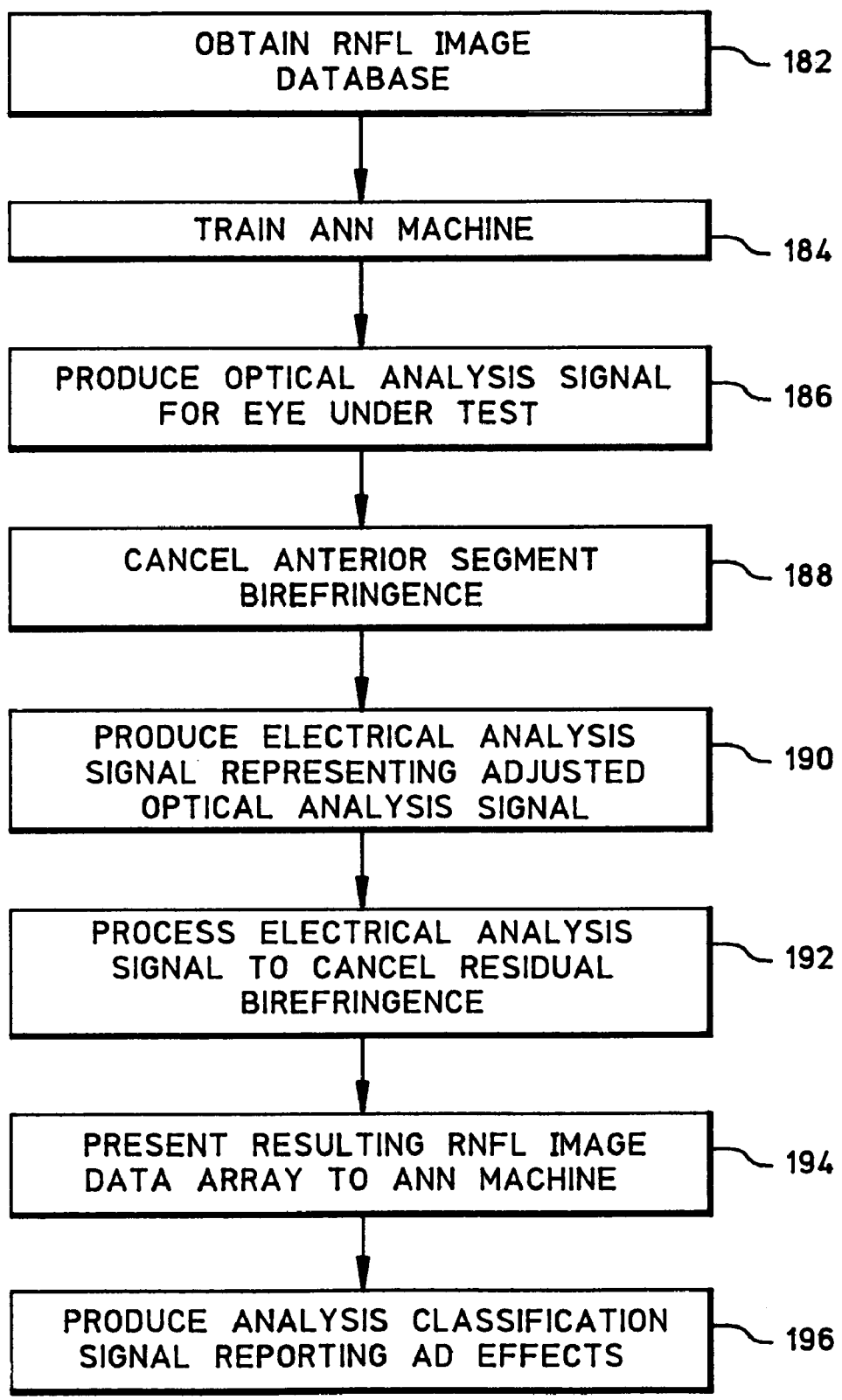
FIG. 3 is a flow chart illustrating an exemplary embodiment of the method of this invention.

FIG. 3 is a flow chart illustrating an exemplary embodiment of the method of this invention. The procedure begins with the step 182 where RNFL image data arrays are obtained for a number of eyes with and without effects of AD. In the next step 184, the ANN machine is trained to distinguish the effects of AD in RNFL image data arrays stored in a database. In step 186, an optical analysis signal is produced representing the birefringence of the biological structures between the exterior of the eye and the posterior surface of the retinal layer in the interior of the eye. In the next step 188, the optical analysis signal is adjusted to cancel the effects of birefringence in the biological segments anterior to the retinal layer. In step 190, an electrical analysis signal is produced representing the adjusted optical analysis signal. In step 192, the electrical analysis signal is processed to cancel the effects of residual birefringence in the exterior optical elements of the ophthalmological polarimeter. Finally, the resulting electrical analysis signal (representing a RNFL image data array) is presented to the ANN machine in the step 194 and an analysis classification signal is produced in the step 196 representing the contribution of AD to the birefringence of the retinal layer that best corresponds to the relationship of the RNFL data array to the database of RNFL image data arrays.

Clearly, other embodiments and modifications of this invention may occur readily to those of ordinary skill in the art in view of these teachings. Therefore, this invention is to be limited only by the following claims, which include all such embodiments and modifications when viewed in conjunction with the above specification and accompanying drawing.

We claim:

1. A method for detecting the effects of Alzheimer's disease in the interior of an eye having a pupil, comprising the steps of:
   (a) producing an optical analysis signal representing the birefringence of biological segments between the exterior of the eye and a posterior surface in a retinal layer in the interior of the eye;
   (b) adjusting the optical analysis signal to cancel the effects of birefringence in the biological segments anterior to the retinal layer;
   (c) passing the adjusted optical analysis signal through one or more optical elements exterior to the eye;
   (d) producing an electrical analysis signal representing the adjusted optical analysis signal;
   (e) processing the electrical analysis signal to cancel the effects of residual birefringence in the one or more optical elements exterior to the eye; and
   (f) producing an analysis classification signal representing the contribution of Alzheimer's disease to the birefringence of the retinal layer corresponding to the relationship of the electrical analysis signal to an analysis signal database.

2. The method of claim 1 further comprising the steps of:
   (a.1) producing an optical diagnostic signal having a predetermined polarization state;
   (a.2) directing the optical diagnostic signal into the eye through the pupil, such that the optical diagnostic signal is reflected from the posterior surface of the retinal layer back through the pupil as a first reflected optical diagnostic signal; and
   (a.3) passing the first reflected optical diagnostic signal through a half-wave retarder along an optical beam axis to produce the optical analysis signal.

3. The method of claim 2 further comprising the steps of:
   (b.1) directing the optical diagnostic signal into the eye through the pupil, such that the optical diagnostic signal is reflected from the anterior surface of the retinal layer back through the pupil as a second reflected optical diagnostic signal;
   (b.2) passing the second reflected optical diagnostic signal through a variable birefringence element;
   (b.3) adjusting the variable birefringence element to realign the polarization state of the second reflected optical diagnostic signal with respect to the predetermined polarization state of the optical diagnostic signal; and (b.4) passing the optical analysis signal through the variable birefringence element to produce the adjusted optical analysis signal.

4. The method of claim 3 further comprising the steps of:

(d.1) producing an electrical signal having a magnitude S representing the polarization state of the adjusted optical analysis signal;

(e.1) rotating the half-wave retarder about the optical beam axis over a substantially forty-five (45) degree range within which the electrical signal magnitude S varies between two extrema; and (e.2) averaging a plurality of electrical signal magnitude extrema obtained during rotation of the half-wave retarder over a substantially one-hundred-and-eighty (180) degree range to produce mean electrical signal magnitude extrema $[\overline{S}_{max}, \overline{S}_{min}]$ representing the electrical analysis signal.

5. The method of claim 4 further comprising the steps of:

(f.1) training an artificial neural network to produce a classification signal responsive to each of a plurality of analysis database signals each representing the birefringence of the retinal layer in an eye; and (f.2) presenting the electrical analysis signal to the trained artificial neural network, thereby producing the analysis classification signal.

6. The method of claim 2 further comprising the steps of:

(d.1) producing an electrical signal having a magnitude S representing the polarization state of the adjusted optical analysis signal;

(e.1) rotating the half-wave retarder about the optical beam axis over a substantially forty-five (45) degree range within which the electrical signal magnitude S varies between two extrema; and (e.2) averaging a plurality of electrical signal magnitude extrema obtained during rotation of the half-wave retarder over a substantially one-hundred-and-eighty (180) degree range to produce mean electrical signal magnitude extrema $[\overline{S}_{max}, \overline{S}_{min}]$ representing the electrical analysis signal.

7. The method of claim 1 further comprising the steps of:

(f.1) training an artificial neural network to produce a classification signal responsive to each of a plurality of analysis database signals each representing the birefringence of the retinal layer in an eye; and (f.2) presenting the electrical analysis signal to the trained artificial neural network, thereby producing the analysis classification signal.

8. The method of claim 7 further comprising the steps of:

(f.1.1) training the artificial neural network to produce a first classification signal responsive to each of a first plurality of analysis database signals each representing the birefringence of a retinal layer known to be affected by Alzheimer's disease; and (f.1.2) training the artificial neural network to produce a second classification signal responsive to each of a second plurality of analysis database signals each representing the birefringence of a retinal layer known to be unaffected by Alzheimer's disease.

9. The method of claim 7 wherein the artificial neural network includes a support vector machine.

10. A system for detecting the effects of Alzheimer's disease in the interior of an eye having a pupil, comprising:

scanning polarimeter means for producing an optical analysis signal representing the birefringence of biological segments of the eye between the exterior of the eye and a posterior surface of a retinal layer in the interior of the eye;

variable retarder means for adjusting the optical analysis signal to remove the effects of birefringence of the biological segments anterior to the retinal layer;

one or more optical elements exterior to the eye for directing the optical analysis signal;

detector means for producing an electrical analysis signal representing the adjusted optical analysis signal;

processor means coupled to the detector means for canceling the effects on the electrical analysis signal of residual birefringence in the one or more optical elements exterior to the eye; and artificial neural network means for producing an analysis classification signal representing the contribution of Alzheimer's disease to the birefringence of the retinal layer corresponding to the relationship of the electrical analysis signal to an analysis signal database.

11. The system of claim 10 further comprising:

optical source means for producing an optical diagnostic signal having a predetermined polarization state;

optics means coupled to the optical source means for directing the optical diagnostic signal into the eye through the pupil, such that the optical diagnostic signal is reflected from the posterior surface of the retinal layer back through the pupil as a first reflected optical diagnostic signal; and half-wave retarder means disposed at an optical beam axis for biasing the polarization state of the reflected optical diagnostic signal from the pupil to produce the optical analysis signal.

12. The system of claim 11 further comprising:

second optics means coupled to the optical source means for directing the optical diagnostic signal into the eye through the pupil, such that the optical diagnostic signal is reflected from the anterior surface of the retinal layer back through the pupil as a second reflected optical diagnostic signal; and a variable birefringence element for realigning the polarization state of the second reflected optical diagnostic signal with respect to the predetermined polarization state of the optical diagnostic signal to produce the adjusted optical analysis signal.

13. The system of claim 12 further comprising:

optical polarization detector means for collecting the adjusted optical analysis signal to produce an electrical signal S having a magnitude representing the polarization state of the adjusted optical analysis signal;

rotator means for rotating the half-wave retarder means about the optical beam axis over a substantially forty-five (45) degree range within which the electrical signal S magnitude varies between two extrema; and logic means for averaging a plurality of electrical signal magnitude extrema obtained during rotation of the half-wave retarder means over a substantially one-hundred-and-eighty (180) degree range to produce mean electrical signal magnitude extrema $[\overline{S}_{max}, \overline{S}_{min}]$ representing the electrical analysis signal.

14. The system of claim 13 further comprising: back-propagation training means for training the artificial neural network means to produce a classification signal responsive to each of a plurality of analysis database signals each representing the birefringence of the retinal layer in an eye.

15. The system of claim 11 further comprising:

optical polarization detector means for collecting the adjusted optical analysis signal to produce an electrical signal S having a magnitude representing the polarization state of the adjusted optical analysis signal;

rotator means for rotating the half-wave retarder means about the optical beam axis over a substantially forty-five (45) degree range within which the electrical signal S magnitude varies between two extrema; and logic means for averaging a plurality of electrical signal magnitude extrema obtained during rotation of the half-wave retarder means over a substantially one-hundred-and-eighty (180) degree range to produce mean electrical signal magnitude extrema [$\overline{S}_{max}, \overline{S}_{min}$] representing the electrical analysis signal.

16. The system of claim 10 further comprising: back-propagation training means for training the artificial neural network means to produce a classification signal responsive to each of a plurality of analysis database signals each representing the birefringence of the retinal layer in an eye.

17. The system of claim 16 further comprising:

means for training the artificial neural network means to produce a first classification signal responsive to each of a first plurality of analysis database signals each representing the birefringence of a retinal layer known to be affected by Alzheimer's disease; and means for training the artificial neural network means to produce a second classification signal responsive to each of a second plurality of analysis database signals each representing the birefringence of a retinal layer known to be unaffected by Alzheimer's disease.

18. The system of claim 16 wherein the artificial neural network means includes a support vector machine.

* * * * *